Aug. 20, 1957 E. S. BOERNER Plant Pat. 1,636
CHRYSANTHEMUM PLANT
Filed Dec. 5, 1956
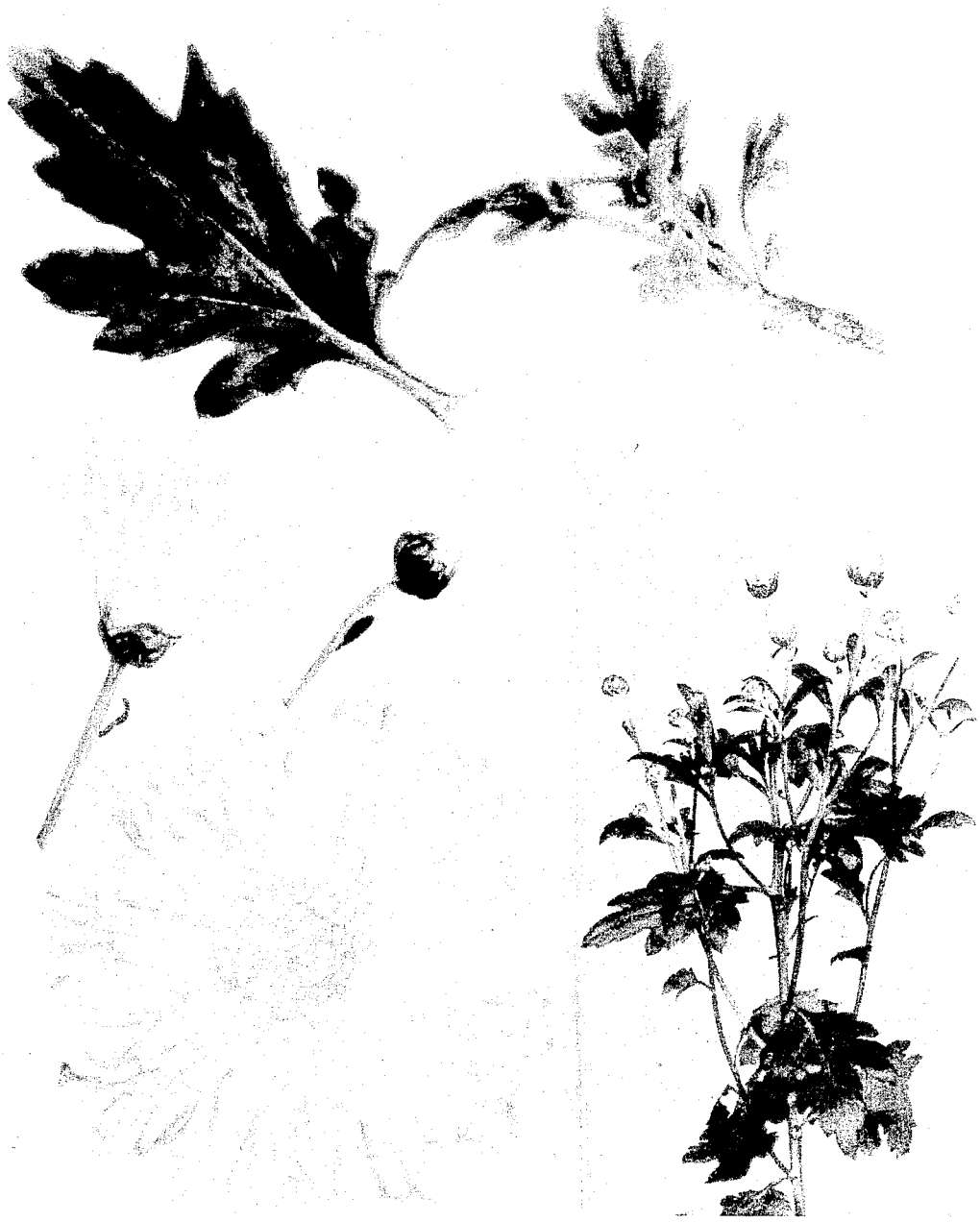
Inventor.
E. S. Boerner
By: Robert Cobb
Attorneys.

United States Patent Office

Plant Pat. 1,636
Patented Aug. 20, 1957

1,636

CHRYSANTHEMUM PLANT

Eugene S. Boerner, Newark, N. Y., assignor to Jackson & Perkins Company, Newark, N. Y., a corporation of New York Application December 5, 1956, Serial No. 626,564

1 Claim. (Cl. 47—60)

The present invention relates to a new and distinct variety of chrysanthemum plant of the decorative type, which was originated by me by crossing the variety "Goldfinch" (Plant Patent No. 1,166) with the variety "Cockatoo" (Plant Patent No. 1,171).

The primary objective of this breeding was to produce a new chrysanthemum variety which bears flowers of the large, decorative type comparable to those of the parent variety "Cockatoo," but having a golden color comparable to that of the parent variety "Goldfinch." This objective was fully achieved, as evidenced by the following characteristics which are outstanding in my new variety:

(1) The large size of the flowers;

(2) The decorative shape of the flowers and their incurved centers; and (3) The distinctive Lemon Yellow, lightly overcast with Apricot Yellow, general color tonality of the flowers.

The foregoing characteristics and distinctions definitely differentiate my new variety from its parents, as well as from all other varieties of its class of which I am aware, and asexual reproduction of the new variety by both top cuttings and underground runners, as performed at Newark, New York, shows that these characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character, and also shows a typical specimen plant in black-and-white which is illustrative of the form and habit of growth of the plant.

The following is a detailed description of my new variety, with color terminology in accordance with Ridgway's Color Standards and Nomenclature, as based upon observations of specimens grown outdoors at Newark, New York, near mid-morning in the latter part of September:

Parentage: "Goldfinch" × "Cockatoo."

Classification: Decorative type, with incurved center.

Growth: Firmly upright; attains height of 30 inches.

Cold resistance: Plant is very winter-hardy in northern New York, and flowers are frost-resistant.

Blooming period: In the Newark, New York, climatic area, blooming usually begins about September 20th and continues until freezing weather.

*Flower*

Bud:

*Color.*—When sepals first divide—Apricot Yellow, Plate 4. When petals begin to unfurl—Light Cadmium, Plate 4. When half-blown: inside of petals—Lemon Chrome, Plate 4; reverse of petals—Lemon Chrome, Plate 4, lightly overcast with Light Cadmium, Plate 4.

*Peduncle.*—Strong. Color—Light Cress Green, Plate 31.

Bloom:

*Size.*—From 5 to 5½ inches.

*Stem.*—Strong; normal.

*Form.*—Decorative, with incurved center.

*Petalage.*—Double.

*Color.*—Center of flower—Light Cadmium, Plate 4, lightly overcast with Lemon Chrome, Plate 4. Outer petals—Pale Lemon Yellow, Plate 4, lightly overcast with Empire Yellow, Plate 4. Base of petals—Clear Dull Green Yellow, Plate 17. Inside of petals—Lemon Yellow, Plate 4, lightly overcast with Apricot Yellow, Plate 4. Reverse of petals—Picric Yellow, Plate 4.

*Petals.*—Texture—thick. Form—double; long.

*Fragrance.*—Characteristic chrysanthemum.

*Plant*

Form: Upright.

Growth: Vigorous; bushy.

Foliage:

*Size.*—Medium large.

*Quantity.*—Normal.

*Color.*—Upper side—Dark Cress Green, Plate 31. Reverse side—Light Cress Green, Plate 31.

*Texture.*—Leathery.

I claim:

A new and distinct variety of chrysanthemum plant of the decorative type with incurved center, substantially as herein shown and described, characterized particularly as to novelty by the relatively large size and distinctive decorative shape of its flowers, and by the distinctive Lemon Yellow, lightly overcast with Apricot Yellow, general color tonality of its flowers.

No references cited.